United States Patent [19]

Carey et al.

[11] Patent Number: 4,743,155
[45] Date of Patent: May 10, 1988

[54] CHIP SAMPLING UNIT

[75] Inventors: Gerald G. Carey, Paris, Tex.; Curtis W. Stacey, Idabel; Bernie M. Baldwin, Valliant, both of Okla.

[73] Assignee: Weyerhaeuser Company, Tacoma, Wash.

[21] Appl. No.: 876,511

[22] Filed: Jun. 20, 1986

[51] Int. Cl.$^4$ .............................................. B65F 9/00
[52] U.S. Cl. .................................. 414/356; 198/537; 73/863.51
[58] Field of Search ............... 414/355, 356, 371, 572, 414/574, 581; 198/537, 716, 735; 73/863.41, 863.42, 863.51, 863.52, 863.56

[56] References Cited

U.S. PATENT DOCUMENTS

| | | | |
|---|---|---|---|
| 1,223,544 | 4/1917 | Wendell | 198/537 X |
| 1,407,926 | 2/1922 | Case | 414/356 X |
| 1,802,856 | 4/1931 | Wiesenthal | 414/356 |
| 2,533,090 | 12/1950 | Bur | 73/863.42 |
| 2,578,849 | 12/1951 | Small | 414/574 X |
| 4,051,948 | 10/1977 | Sackett | 198/735 X |
| 4,221,520 | 9/1980 | Bartley | 414/356 X |
| 4,574,645 | 3/1986 | Allen et al. | 73/863.51 |

OTHER PUBLICATIONS

Dravo Corporation Catalogue, pp. 2143-2147.
Pulp & Paper, Technical Section, Monograph #5, "Chip Quality", Editor: J. V. Hatton, 1979, Joint Technical Committee of the Paper Industry, p. 181.

Primary Examiner—Dave W. Arola

[57] ABSTRACT

A chip sampling unit and method for obtaining a representative sample from a chip transporting unit such as a railcar or trailer.

5 Claims, 1 Drawing Sheet

CHIP SAMPLING UNIT

FIELD

This invention relates to an apparatus for obtaining a representative sample of wood chips from a chip transporting unit such as a railcar or trailer.

PRIOR PRACTICE

Wood chips are used in both pulping and in the manufacture of certain types of board products. Chips often are manufactured at one location and transported to the place of use by a transporting unit such as a railcar or truck trailer. The transporting unit is open topped and covered by a tarpaulin during transport. At the place of use the transporting units are uncovered and are unloaded by a rotary car dumper. Two such dumpers are shown in the Dravo Corp. catalog, pages 2143-2147, and on page 181 of the Monograph No. 5, Chip Quality, J. V. Hatton, editor, published 1979 by the Joint Technical Committee of the Paper Industry. The Dravo Corporation catalog shows the Dravo Wellman Rotary Car Dumper, and the Monograph shows the rotary car dumper at the Weyerhaeuser Company Valliant, Okla., pulp mill.

The unloaders hold the car or trailer in position in relationship to the unloader and rotate the open topped transporting unit to dump the chips from the transporting unit. It is necessary to determine the various sizes of material in the car to understand how to handle the chips during processing. The sizes may range from very large to dust, and if there is too large an undesirable fraction then the chips may have to be classified before processing to remove the undesirable fraction.

There is always a question as to whether the sample obtained is representative of the chips in the transporting unit. A standard method of obtaining a sample is to have a chain and flights on the bottom of the pit or area where the chips are dumped. This would obtain a sample from the bottom of the pile which would usually represent the top of the transporting unit.

Another method is to take a grab sample from the transporting unit. However, this represents a finite spot in the unit and not an average sample.

SUMMARY OF THE INVENTION

The inventors wanted to obtain a sample which would be more representative of the chips in the unit and decided that one way would be to take a sample that represented a vertical core of the chips in the transporting unit. This would then be a sample of the larger particles which would tend to remain at the top of the transporting unit as well as the finer material which would tend to migrate to the bottom of the transporting unit during travel. There would still be some inconsistency because it would be impossible to sample the entire chip load but it would be better than before because it would sample the chip load from top to bottom and eliminate the variations caused by the vibration of the chip load during transportation.

They placed a catching or sampling bin in the path of travel of the chips as they fell from the overturned trasport unit to the chip receiving area. The bin was placed with an upward opening which was aligned the the path of travel of the chips from the center of the transporting unit. It was decided arbitrarily to use the center of the transporting unit as a representive chip core. The bin opening may be placed at any desired location in the chip fall.

The bin has a lower opening which allows the chips in the bin to drop onto a conveyor which transports the chips from the site. This constant removal of chips from the bottom of the bin allows new chips from the vertical core to fall into the bin and a sample from the entire top to bottom core to be obtained. It was found during testing that the conveyor had to be moved at a linear speed of at least one foot a second if a representative sample was to be obtained. At slower speeds the the bin tended to fill and the larger particles would either drop out of the bin, causing the sample to be unrepresentative.

DESCRIPTION OF THE PREFERRED EMBODIMENT

Figure 1:
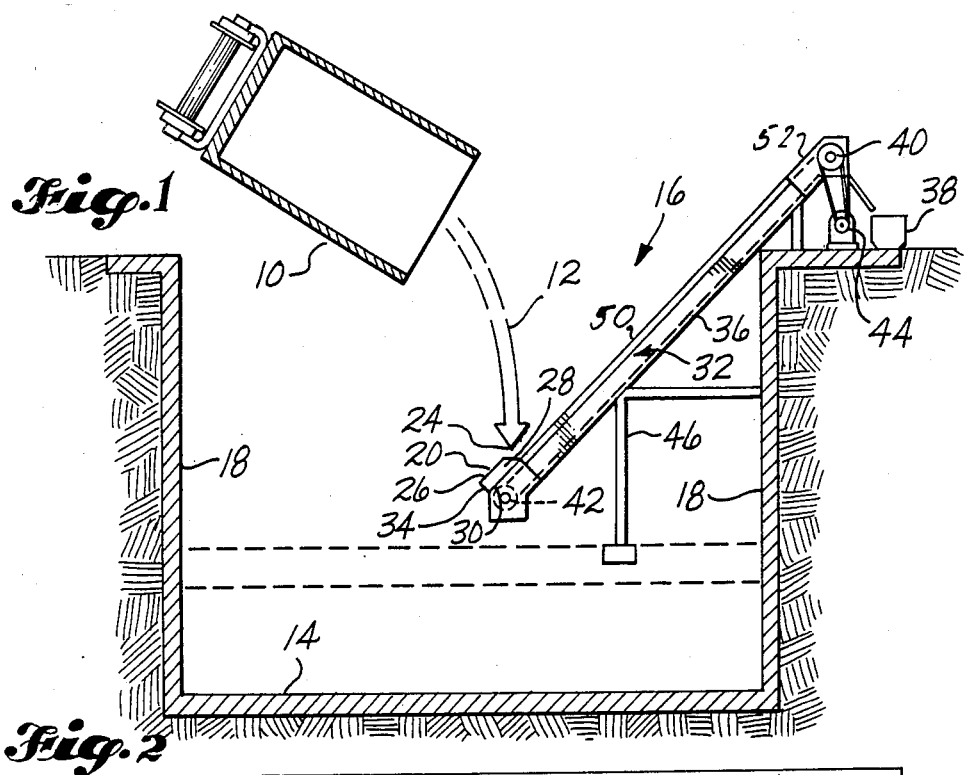
FIG. 1 is a side view, partially in cross section, showing the chip dumping facility and the chip sampling unit.
Figure 2:
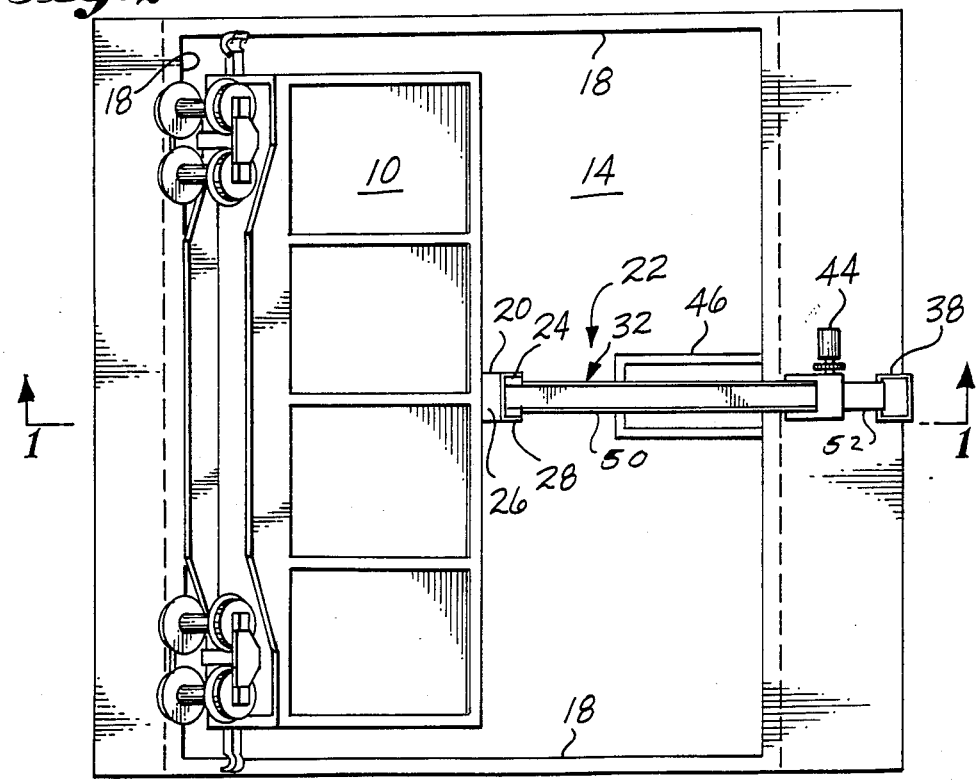
FIG. 2 is a top plan view of the chip dumping facility and the chip sampling unit.

In the drawings the rotary car dumper is not shown in order to show the relationship of the transporting unit and the sampling unit. The transporting unit 10 is held in the rotary car dumper (not shown) and rotated to dump the chips. The arrow 12 represents the path of travel of the chips from the center of the transporting unit. This is shown as being the lengthwise and widthwise center of the transporting unit. The chips from the transporting unit 10 are dumped onto a chip receiving area 14. In the present drawings the chip receiving area 14 is the bottom wall of the chip dumping pit 16. The chip dumping pit 16 has the bottom wall 14 land the side walls 18.

The bin 20 of the chip sampling unit 22 is located between the open top of the transporting unit 10 and the chip receiving area 14. The upper opening 24 of the bin 20 is located in the path of travel of the chips represented by the arrow 12. The bin 20 has, besides the upper opening 24, a front or upper wall 26, side walls 28, and a rear opening 30 to a conveyor 32. The lower side 34 of the bin 20 may be either closed if the entire sample is to be taken from the bin, or open if only a portion of the sample is to be taken from the bin.

The conveyor is a chain 36 with flights which passes through two rectangular tubes 50 and 52. The flights carry the chips from the opening 30 to a second sampling bin 38. A pair of sprockets, drive sprocket 40 and idler sprocket 42, and motor 44 drive the conveyor. The conveyor is enclosed in the two rectangular tubes 50 and 52 so that chips may enter the conveyor through the rear bin opening 30. The chips are carried on the center wall of the conveyor by the chain flights. The conveyor is preferably at an angle to the horizontal of slightly greater than 45 degrees.

In a preferred unit the distance between the sprockets is 200 inches, the horizontal distance between the sprockets is 145 inches and the vertical distance between the sprockets is 155 inches. The flights are one inch high and approximately 18 inches apart. The rectangular tubes 50 and 52 for the conveyor are each 8 inches high and 16 inches wide. The speed of travel is greater than one foot per second. It usually is between one and five feet per second. In the preferrred unit it is one and one-half feet per second. The installation will depend upon the actual configuration of the car dumping facility.

A suitable frame 46 holds the sampling unit in place.

Table 1 compares samples taken from the sampler (Sampler) with samples taken by hand (Transfer Point) to compare the and determine if the sampling unit was obtaining a representative sample. The samples may not have been paired samples. It was found that that was no statistical difference. The units in the tables are Over L (over length; material that passes through a 45 mm hole); Over Th (over thick; remaining material that passes through a 10 mm slot); Acc (accepts; +⅜ inch, remaining material that does not pass through a ⅜ inch hole); Pin1 (matchlike material; +¼ inch, remaining material that does not pass through a ¼ inch hole); Pin2 (matchlike material; +3/16 inch, remaining material that does not pass through a 3/16 inch hole); Fines (the rest); and bark (bark).

TABLE I

| Date | Over L | Over TH | Acc | Pin 1 | Pin 2 | Fines | Bark | Dry Wt. |
|---|---|---|---|---|---|---|---|---|
| | | | | Sampler | | | | |
| | 2.9 | 3.9 | 80.4 | 7.2 | 2.3 | 1.8 | 1.5 | 46.9 |
| | 2 | 5.7 | 80.4 | 6.3 | 2 | 1.5 | 2.1 | 46.3 |
| | 2 | 6.5 | 75.2 | 9 | 3.2 | 2.1 | 1.9 | 47.8 |
| | 3.3 | 4.7 | 79.6 | 7.6 | 2 | 1.6 | 1.2 | 46.7 |
| | 1.7 | 3 | 84.9 | 6.8 | 2 | 1.4 | 0.2 | 48.8 |
| | 2 | 2.5 | 83.9 | 7.6 | 1.9 | 1.1 | 0.9 | 47.3 |
| | 3 | 2.9 | 84.8 | 5.7 | 1.7 | 1.1 | 0.8 | 47.6 |
| | 3.3 | 4.7 | 82.6 | 6 | 1.7 | 1.2 | 0.6 | 48.5 |
| | 1.8 | 4.9 | 83.2 | 5.7 | 2.4 | 1.7 | 0.2 | 49.6 |
| | 1.1 | 3.8 | 85.3 | 5.3 | 2.6 | 1.8 | 0.1 | 48.3 |
| | 3.1 | 5.6 | 82.3 | 5 | 2.2 | 1.5 | 0.2 | 48.6 |
| | 1.1 | 6 | 85.8 | 3.8 | 1.4 | 1.6 | 0.3 | 48.3 |
| | 4.2 | 7.6 | 78.8 | 5.1 | 2.4 | 1.8 | 0 | 48.1 |
| | 3.2 | 5.1 | 83 | 4.9 | 2.1 | 1.6 | 0.1 | 47 |
| | 0.8 | 3.9 | 73.6 | 12.3 | 5.3 | 4.2 | 0.1 | 50.8 |
| | 0.5 | 0.7 | 87.9 | 6.6 | 2.1 | 1.6 | 0.5 | 50.8 |
| | 2.25 | 4.46875 | 81.98125 | 6.55625 | 2.33125 | 1.725 | 0.66875 | 48.2125 |
| | 1.034408 | 1.649893 | 3.714871 | 1.935190 | 0.864377 | 0.0689655 | 0.654521 | 1.285435 |
| | 16 | 16 | 16 | 16 | 16 | 16 | 16 | 16 |
| | | | | Transfer Point | | | | |
| | 1 | 4 | 81 | 8.3 | 2.7 | 1.7 | 1.2 | 47.6 |
| | 2 | 7.7 | 76.4 | 7.7 | 2.4 | 1.9 | 1.8 | 48.2 |
| | 2.5 | 5.2 | 76.3 | 9 | 2.8 | 2.3 | 2 | 47.1 |
| | 1.3 | 2.9 | 81.3 | 8.9 | 2.5 | 1.7 | 1.4 | 48.1 |
| | 1.1 | 2.5 | 86.3 | 6.5 | 2 | 1.3 | 0.4 | 48.5 |
| | 1.8 | 3.4 | 84 | 6.7 | 1.9 | 1.2 | 1 | 48.5 |
| | 2.9 | 3.9 | 82.6 | 6.7 | 1.7 | 1.2 | 0.9 | 49.8 |
| | 1.6 | 3.8 | 83.5 | 7.3 | 1.9 | 1.2 | 0.7 | 50.4 |
| | 3.6 | 6.4 | 81.2 | 5 | 2.1 | 1.6 | 0.1 | 48.5 |
| | 1.3 | 5.7 | 82.1 | 5.9 | 2.7 | 2.2 | 0.1 | 49.6 |
| | 2.6 | 3.9 | 83.1 | 5.7 | 2.6 | 2 | 0.1 | 49.2 |
| | 2.9 | 10 | 80.2 | 3.6 | 1.4 | 1.3 | 0.4 | 50 |
| | 0.5 | 8 | 82.2 | 5.1 | 2.3 | 1.8 | 0.2 | 48.4 |
| | 3.4 | 6.6 | 81.2 | 4.9 | 2.1 | 1.6 | 0.2 | 48.4 |
| | 0.7 | 3.2 | 86 | 6.6 | 1.8 | 1.2 | 0.5 | 51.3 |
| | 2.7 | 4.3 | 85.7 | 5.2 | 1.1 | 0.8 | 0.2 | 48.7 |
| **** | 1.99375 | 5.09375 | 82.06875 | 6.44375 | 2.125 | 1.5625 | 0.7 | 48.89375 |
| **** | 0.941055 | 2.061694 | 2.804398 | 1.484069 | 0.472361 | 0.402919 | 0.603116 | 1.051468 |
| **** | 16 | 16 | 16 | 16 | 16 | 16 | 16 | 16 |
| T-Stat | 0.732968 | −0.94675 | −0.07519 | 0.184521 | 0.837542 | 0.813792 | −0.14044 | −1.64087 |

We claim:

1. A wood chip sampling unit for sampling wood chips from a descending flow of wood chips to a chip receiving area comprising
   a conveyor,
   means for moving said conveyor at a lineal speed of at least one foot per second,
   means spaced from and covering said conveyor to prevent unwanted chips from entering said conveyor,
   a sampling bin attached to the upper face of said conveyor covering means,
   said sampling bin having an upper opening for receiving said wood chips,
   a lower side opposite said upper opening,
   a front face extending between said upper opening and said lower side,
   side faces extending between said upper opening and said lower side, and
   a rear opening to said conveyor opposite said front face, said rear opening allowing the chips to move from said bin to said conveyor.

2. The sampling unit of claim 1 in which the lower side of said sampling bin is closed.

3. The sampling unit of claim 1 in which the lower side of said sampling bin is open to allow chips to pass from said bin.

4. A wood chip sampling unit for a means for rotating and dumping wood chips from a chip transporting unit comprising
   a chip receiving area,
   means above said chip receiving area for rotating and dumping chips from a chip transporting means,
   said chips passing through a path of travel from said chip transporting unit to said receiving area,
   a conveyor,
   means for moving said conveyor at a lineal speed of at least one foot per second,
   means spaced from and covering said conveyor to prevent unwanted chips from entering said conveyor, a sampling bin attached to the upper face of said conveyor covering means, said sampling bin having an upper opening for receiving said wood chips, a lower side opposite said upper opening, a front face extending between said upper opening and said lower side, side faces extending between said upper opening and said lower side, and a rear opening to said conveyor opposite said front face, said rear opening allowing the chips to move from said bin to said conveyor.

5. The unit of claim 4 in which said bin upper opening is located in the path of travel of the center of said transporting unit.

* * * * *

UNITED STATES PATENT AND TRADEMARK OFFICE
CERTIFICATE OF CORRECTION

PATENT NO. : 4,743,155

DATED : May 10, 1988

INVENTOR(S) : Carey et al.

It is certified that error appears in the above-identified patent and that said Letters Patent is hereby corrected as shown below:

In TABLE I, the column labeled "Fines", reading down, the figure "0.0689655" should read --0.689655--;

Signed and Sealed this

Twenty-eighth Day of March, 1989

Attest:

DONALD J. QUIGG

Attesting Officer

Commissioner of Patents and Trademarks